US006235510B1

(12) United States Patent
Lark et al.

(10) Patent No.: US 6,235,510 B1
(45) Date of Patent: May 22, 2001

(54) PPGANTASE-T6

(75) Inventors: Michael W Lark, Devon; Sanjay Kumar, Audubon; Marion M Van Horn, Folsom, all of PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/376,856

(22) Filed: Aug. 18, 1999

(51) Int. Cl.$^7$ .............................. C12P 21/06; C12N 9/10; C12N 1/20; C12N 15/00

(52) U.S. Cl. ..................... 435/193; 435/69.1; 435/72; 435/97; 435/100; 435/101; 435/105; 435/193; 435/254.2; 435/320.1; 435/440; 536/23.2; 530/350

(58) Field of Search ............................ 435/69.1, 72, 97, 435/100, 101, 105, 193, 254.2, 320.1, 440; 536/23.2, 23.4; 530/350

(56) References Cited

PUBLICATIONS

Bennett et al., "Cloning of a Human UDP–N–Acetyl–α–D–Galactosamine: Polypeptide N–Acetylgalactosaminyltransferase That Complements Other GalNAc–Transferases in Complete O–Glycosylation of the MUC1 Tandem Repeat", Jour. Bio Chem. vol. 273, pp. 30472–30481 (1998).
GenBank Accession No. Y08564.
GenBank Accession No. AA368180.
GenBank Accession No. AA971319.
GenBank Accession No. AA236602.
GenBank Accession No. AI275884.
GenBank Accession No. AI378176.
GenBank Accession No. AA055174.
GenBank Accession No. AA055179.
GenBank Accession No. AI207963.
Hagen et al., "cDNA Cloning and Expression of a Noval UDP–N–acetyl–Dgalactosamine:Polypeptide N–Acetylgalactosaminyltransferase", *The Journal of Biological Chemistry*, vol. 272, No. 21, pp. 13843–13848 (May 1997).
Hagen et al., "Cloning and Expression of a Noval, Tissue Specifically Expressed Member of tghe UDP–Galnac:Polypeptide N–Acetylgalactosaminyltransferase Family", *The Journal of Biological Chemistry*, vol. 273, No. 42, pp. 27749–27754 (Oct. 1998).
Hagen et al., "cDNA Cloning and Expression of a Family of UDP–N–acetyl–D–Galactosamine: Polypeptide N–Acetylgalactosaminyltransferase Sequence Homologs from Caenorhabditis elegans", *The Journal of Biological Chemistry*, vol. 273, No. 14 pp. 8268–8277 (Apr. 1998).

*Primary Examiner*—Rebecca E. Prouty
*Assistant Examiner*—Manjunath N. Rao
(74) *Attorney, Agent, or Firm*—William T. Han; Ratner & Prestia; William T. King

(57) ABSTRACT ppGaNTase-T6 polypeptides and polynucleotides and methods for producing such polypeptides by recombinant techniques are disclosed. Also disclosed are methods for utilizing ppGaNTase-T6 polypeptides and polynucleotides in diagnostic assays.

12 Claims, No Drawings

SEQUENCE LISTING

<160> NUMBER OF SEQ ID NOS: 2

<210> SEQ ID NO 1
<211> LENGTH: 1920
<212> TYPE: DNA
<213> ORGANISM: HOMO SAPIENS

<400> SEQUENCE: 1

| | | | | | |
|---|---|---|---|---|---|
| atgctcctaa | ggaagcgata | caggcacaga | ccatgcagac | tccagttcct | cctgctgctc | 60 |
| ctgatgctgg | gatgcgtcct | gatgatggtg | gcgatgttgc | accctcccca | ccacaccctg | 120 |
| caccagactg | tcacagccca | agccagcaag | cacagccctg | aagccaggta | ccgcctggac | 180 |
| tttggggaat | cccaggattg | ggtactggaa | gctgaggatg | agggtgaaga | gtacagccct | 240 |
| ctggagggcc | tgccacccct | tatctcactg | cgggaggatc | agctgctggt | ggccgtggcc | 300 |
| ttaccccagg | ccagaaggaa | ccagagccag | ggcaggagag | gtgggagcta | ccgcctcatc | 360 |
| aagcagccaa | ggaggcagga | taaggaagcc | ccaaagaggg | actgggggc | tgatgaggac | 420 |
| ggggaggtgt | ctgaagaaga | ggagttgacc | ccgttcagcc | tggacccacg | tggcctccag | 480 |
| gaggcactca | gtgcccgcat | ccccctccag | agggctctgc | ccgaggtgcg | gcacccactg | 540 |
| tgtctgcagc | agcaccctca | ggacagcctg | cccacagcca | gcgtcatcct | ctgtttccat | 600 |
| gatgaggcct | ggtccactct | cctgcggact | gtacacagca | tcctcgacac | agtgcccagg | 660 |
| gccttcctga | aggagatcat | cctcgtggac | gacctcagcc | agcaaggaca | actcaagtct | 720 |
| gctctcagcg | aatatgtggc | caggctggag | ggggtgaagt | tactcaggag | caacaagagg | 780 |
| ctgggtgcca | tcagggcccg | gatgctgggg | gccaccagag | ccaccgggga | tgtgctcgtc | 840 |
| ttcatggatg | cccactgcga | gtgccaccca | ggctggctgg | agcccctcct | cagcagaata | 900 |
| gctggtgaca | ggagccgagt | ggtatctccg | gtgatagatg | tgattgactg | gaagactttc | 960 |
| cagtattacc | cctcaaagga | cctgcagcgt | ggggtgttgg | actggaagct | ggatttccac | 1020 |
| tgggaacctt | tgccagagca | tgtgaggaag | gccctccagt | ccccccataag | ccccatcagg | 1080 |
| agccctgtgg | tgcccggaga | ggtggtggcc | atggacagac | attacttcca | aaacactgga | 1140 |
| gcgtatgact | ctcttatgtc | gctgcgaggt | ggtgaaaacc | tcgaactgtc | tttcaaggcc | 1200 |
| tggctctgtg | gtggctctgt | tgaaatcctt | ccctgctctc | gggtaggaca | catctaccaa | 1260 |
| aatcaggatt | cccattcccc | cctcgaccag | gaggccaccc | tgaggaacag | ggttcgcatt | 1320 |
| gctgagacct | ggctggggtc | attcaaagaa | accttctaca | agcatagccc | agaggccttc | 1380 |
| tccttgagca | aggctgagaa | gccagactgc | atggaacgct | tgcagctgca | aaggagactg | 1440 |
| ggttgtcgga | cattccactg | gtttctggct | aatgtctacc | ctgagctgta | cccatctgaa | 1500 |
| cccaggccca | gtttctctgg | aaagctccac | aacactggac | ttgggctctg | tgcagactgc | 1560 |
| caggcagaag | gggacatcct | ggctgtccc | atggtgttgg | ctccttgcag | tgacagccgg | 1620 |
| cagcaacagt | acctgcagca | caccagcagg | aaggagattc | actttggcag | cccacagcac | 1680 |
| ctgtgctttg | ctgtcaggca | ggagcaggtg | attcttcaga | actgcacgga | ggaaggcctg | 1740 |
| gccatccacc | agcagcactg | ggacttccag | gagaatggga | tgattgtcca | cattctttct | 1800 |
| gggaaatgca | tggaagctgt | ggtgcaagaa | acaataaag | atttgtacct | gcgtccgtgt | 1860 |
| gatggaaaag | cccgccagca | gtggcgtttt | gaccagatca | atgctgtgga | tgaacgatga | 1920 |

<210> SEQ ID NO 2
<211> LENGTH: 639

```
<212> TYPE: PRT
<213> ORGANISM: HOMO SAPIENS

<400> SEQUENCE: 2

Met Leu Leu Arg Lys Arg Tyr Arg His Arg Pro Cys Arg Leu Gln Phe
 1               5                  10                  15

Leu Leu Leu Leu Leu Met Leu Gly Cys Val Leu Met Met Val Ala Met
                20                  25                  30

Leu His Pro Pro His His Thr Leu His Gln Thr Val Thr Ala Gln Ala
                35                  40                  45

Ser Lys His Ser Pro Glu Ala Arg Tyr Arg Leu Asp Phe Gly Glu Ser
    50                  55                  60

Gln Asp Trp Val Leu Glu Ala Glu Asp Glu Gly Glu Glu Tyr Ser Pro
65                  70                  75                  80

Leu Glu Gly Leu Pro Pro Phe Ile Ser Leu Arg Glu Asp Gln Leu Leu
                85                  90                  95

Val Ala Val Ala Leu Pro Gln Ala Arg Arg Asn Gln Ser Gln Gly Arg
                100                 105                 110

Arg Gly Gly Ser Tyr Arg Leu Ile Lys Gln Pro Arg Arg Gln Asp Lys
            115                 120                 125

Glu Ala Pro Lys Arg Asp Trp Gly Ala Asp Asp Gly Glu Val Ser
130                 135                 140

Glu Glu Glu Glu Leu Thr Pro Phe Ser Leu Asp Pro Arg Gly Leu Gln
145                 150                 155                 160

Glu Ala Leu Ser Ala Arg Ile Pro Leu Gln Arg Ala Leu Pro Glu Val
                165                 170                 175

Arg His Pro Leu Cys Leu Gln Gln His Pro Gln Asp Ser Leu Pro Thr
                180                 185                 190

Ala Ser Val Ile Leu Cys Phe His Asp Glu Ala Trp Ser Thr Leu Leu
                195                 200                 205

Arg Thr Val His Ser Ile Leu Asp Thr Val Pro Arg Ala Phe Leu Lys
                210                 215                 220

Glu Ile Ile Leu Val Asp Asp Leu Ser Gln Gln Gly Gln Leu Lys Ser
225                 230                 235                 240

Ala Leu Ser Glu Tyr Val Ala Arg Leu Glu Gly Val Lys Leu Leu Arg
                245                 250                 255

Ser Asn Lys Arg Leu Gly Ala Ile Arg Ala Arg Met Leu Gly Ala Thr
                260                 265                 270

Arg Ala Thr Gly Asp Val Leu Val Phe Met Asp Ala His Cys Glu Cys
                275                 280                 285

His Pro Gly Trp Leu Glu Pro Leu Leu Ser Arg Ile Ala Gly Asp Arg
                290                 295                 300

Ser Arg Val Val Ser Pro Val Ile Asp Val Ile Asp Trp Lys Thr Phe
305                 310                 315                 320

Gln Tyr Tyr Pro Ser Lys Asp Leu Gln Arg Gly Val Leu Asp Trp Lys
                325                 330                 335

Leu Asp Phe His Trp Glu Pro Leu Pro Glu His Val Arg Lys Ala Leu
                340                 345                 350

Gln Ser Pro Ile Ser Pro Ile Arg Ser Pro Val Val Pro Gly Glu Val
                355                 360                 365

Val Ala Met Asp Arg His Tyr Phe Gln Asn Thr Gly Ala Tyr Asp Ser
                370                 375                 380

Leu Met Ser Leu Arg Gly Gly Glu Asn Leu Glu Leu Ser Phe Lys Ala
385                 390                 395                 400
```

-continued

```
Trp Leu Cys Gly Gly Ser Val Glu Ile Leu Pro Cys Ser Arg Val Gly
            405                 410                 415

His Ile Tyr Gln Asn Gln Asp Ser His Ser Pro Leu Asp Gln Glu Ala
            420                 425                 430

Thr Leu Arg Asn Arg Val Arg Ile Ala Glu Thr Trp Leu Gly Ser Phe
            435                 440                 445

Lys Glu Thr Phe Tyr Lys His Ser Pro Glu Ala Phe Ser Leu Ser Lys
    450                 455                 460

Ala Glu Lys Pro Asp Cys Met Glu Arg Leu Gln Leu Gln Arg Arg Leu
465                 470                 475                 480

Gly Cys Arg Thr Phe His Trp Phe Leu Ala Asn Val Tyr Pro Glu Leu
                485                 490                 495

Tyr Pro Ser Glu Pro Arg Pro Ser Phe Ser Gly Lys Leu His Asn Thr
                500                 505                 510

Gly Leu Gly Leu Cys Ala Asp Cys Gln Ala Glu Gly Asp Ile Leu Gly
            515                 520                 525

Cys Pro Met Val Leu Ala Pro Cys Ser Asp Ser Arg Gln Gln Gln Tyr
    530                 535                 540

Leu Gln His Thr Ser Arg Lys Glu Ile His Phe Gly Ser Pro Gln His
545                 550                 555                 560

Leu Cys Phe Ala Val Arg Gln Glu Gln Val Ile Leu Gln Asn Cys Thr
                565                 570                 575

Glu Glu Gly Leu Ala Ile His Gln His Trp Asp Phe Gln Glu Asn
            580                 585                 590

Gly Met Ile Val His Ile Leu Ser Gly Lys Cys Met Glu Ala Val Val
        595                 600                 605

Gln Glu Asn Asn Lys Asp Leu Tyr Leu Arg Pro Cys Asp Gly Lys Ala
    610                 615                 620

Arg Gln Gln Trp Arg Phe Asp Gln Ile Asn Ala Val Asp Glu Arg
625                 630                 635
```

PPGANTASE-T6

FIELD OF THE INVENTION

This invention relates to newly identified polypeptides and polynucleotides encoding such polypeptides, to their use in diagnosis and in identifying compounds that may be agonists, antagonists that are potentially useful in therapy, and to production of such polypeptides and polynucleotides.

BACKGROUND OF THE INVENTION

The drug discovery process is currently undergoing a fundamental revolution as it embraces "functional genomics", that is, high throughput genome- or gene-based biology. This approach as a means to identify genes and gene products as therapeutic targets is rapidly superceding earlier approaches based on "positional cloning". A phenotype, that is a biological function or genetic disease, would be identified and this would then be tracked back to the responsible gene, based on its genetic map position.

Functional genomics relies heavily on high-throughput DNA sequencing technologies and the various tools of bioinformatics to identify gene sequences of potential interest from the many molecular biology databases now available. There is a continuing need to identify and characterize further genes and their related polypeptides/proteins, as targets for drug discovery.

Mammalian connective tissues contain proteins, glycoproteins and large complex glycoconjugates, such as proteoglycans. Control of the synthesis, post-translational modification, organization and degradation of these components appears very important in maintaining tissue homeostasis. Uncontrolled matrix deposition or degradation results in loss of tissue function in virtually all known pathology.

Articular cartilage is a matrix-rich, avascular, aneural tissue that allows the fluid articulation of synovial joints. Chondrocytes are the only cells within this tissue and are responsible for cartilage matrix biosynthesis and assembly and also play a role in matrix catabolism in diseases, such as osteoarthritis (OA) and rheumatoid arthritis (RA). Cartilage matrix is rich in carbohydrate-containing proteoglycans as well as glycoproteins. In both OA and RA, there appears to be changes in the synthesis and degradation of the protein cores as well as changes in the glycosylation patterns of these molecules.

One of the major articular cartilage matrix components is the large proteoglycan, aggrecan. Aggrecan is a glycosoaminoglycan (GAG)-rich molecule that contains chondroitin sulfate and keratan sulfate chains as well as N-(asparagine) and O-(serine and threonine) linked oligosaccahrides. The tissue also contains several glycoproteins, some of which are also O-glycosylated.

Chondroitin sulfate is the predominant GAG on aggrecan. It is a repeating polymer of N-acetylgalactosamine and glucuronic acid. These chondroitin sulfate chains are variably sulfated on N-acetylgalactosamine residues in either the 4, 6 or disulfated in both the 4 and 6 positions. In OA, the length of the chondroitin sulfate chains are shorter and the sulfation pattern changes with an increase in 4-sulfation and a reduction in the terminal N-acetylgalactosamine 4,6-disulfation (Plass et al. J. Biol. Chem. 273:12642–12649, 1998). These structural changes in the molecule could result in a matrix with lower water binding capacity and may influence interactions with other matrix components, ultimately resulting in a destabilized matrix.

Keratan sulfate is the other major GAG on aggrecan and is covalently attached to the core protein through either an N- or O-linkage (Hascall and Midura in Keratan sulfate chemistry, biology, chemical pathology 1989 eds. H. Greiling and J. Scott, London: The Biochemical Society, pps 66–75). Serine or threonine post-translational glycosylation to form keratan sulfate is initiated by transfer of N-acetylgalactosamine by specific enzymes. The O-linked keratan sulfate pattern changes in the intraglobular domain of aggrecan with aging (Barry et al., J. Biol. Chem. 270:20516–20524, 1995). One of these variable glycosylation sites is prone to cleavage by the chondrocyte-derived proteinase, aggrecanase (Arner et al, J. Biol. Chem. 274:6594–6601, 1999). Aggrecanase-cleaved aggrecan fragments accumulate at sites of articular cartilage damage in OA and RA (Lark et al., J. Clin. Invest. 100:93–96, 1997) and cleavage activity could be influenced by the glycosylation state of the aggrecan substrate in this intraglobular domain region. Furthermore, keratan sulfate levels appear to be modulated in patients with OA and has been proposed as a potential marker to monitor cartilage matrix turnover (Lohmander, Baillere's Clin. Rhem. 11:711–726, 1997). Changes in the circulating andjoint fluid levels of keratan sulfate could reflect changes in the pattern or levels of enzymes that are responsible for transferring sugar moieties onto protein core. In addition to keratan sulfate, aggrecan contains O-linked oligosaccharides which may influence its ability to interact with other components to maintain a stable extracellular matrix. Careful analysis of 0-linked oligosaccharide changes in aggrecan as cartilage destruction progresses has not been done; however, it is possible that these oligosaccharide patterns could also have profound effects on cartilage matrix structure.

Several UDP-GalNac:polypeptide N-acetylgalactosaminyltransferases (ppGaNTase, EC 2.4.1.41) regulate the initiation of mucin-type O-linked glycosylation where N-acetylgalactosamine is transferred to the hydroxyl group of serine and threonine residues (Clausen and Bennet, Glycobiology 6:635–546, 1996). To date, five members of this family (ppGaNTase-T1, -T2, -T3, -T4 and -T5) have been reported in mammalian cells (Clausen and Bennet, Glycobiology 6:635–546, 1996, Bennet et al. J. Biol. Chem. 273:30472–30481, 1998, Ten Hagen et al. J. Biol. Chem. 273:27749–27754, 1998). Five additional members have been reported in Caenorabditis elegans (Hagen and Nehrke, J. Biol. Chem. 273: 8268–8277, 1998). Present data based on some of the characterized enzymes suggest that there are differences in substrate specificity as well as the expression pattern of these enzymes (Clausen and Bennet, Glycobiology 6:635–546, 1996). Conservation from worms to humans underscores the functional importance and diversity of this family of enzymes. Families of enzymes responsible for carbohydrate addition in glycosaminoglycan synthesis and glycoprotein post-translational modification have been described, and new members of these families continue to emerge. A new member of the UDP-GalNAc:polypeptide N-acetylgalactosaminyltransferase family of enzymes termed ppGaNTase-T6 is described herein.

SUMMARY OF THE INVENTION

The present invention relates to ppGaNTase-T6, in particular ppGaNTase-T6 polypeptides and ppGaNTase-T6 polynucleotides, recombinant materials and methods for their production. Such polypeptides and polynucleotides are of interest in relation to methods of treatment of certain diseases, including, but not limited to, chronic and acute inflammation, rheumatoid arthritis, osteoarthritis, septicemia, autoimmune diseases (e.g., inflammatory bowel disease, psoriasis), transplant rejection, graft vs. host disease, infection, stroke, ischemia, acute respiratory disease syndrome, allergy, asthma, renal disorders, restenosis, fibrosis, brain injury, AIDS, metabolic and other bone diseases (e.g., osteoporosis), cancer (e.g., lymphoproliferative disorders), atherosclerosis, and Alzheimers disease, hereinafter referred to as "diseases of the invention." In a further aspect, the invention relates to methods for identifying agonists and antagonists (e.g., inhibitors) using the materials provided by the invention, and treating conditions associated with ppGaNTase-T6 imbalance with the identified compounds. In a still further aspect, the invention relates to diagnostic assays for detecting diseases associated with inappropriate ppGaNTase-T6 activity or levels.

DESCRIPTION OF THE INVENTION

In a first aspect, the present invention relates to ppGaNTase-T6 polypeptides. Such polypeptides include:
(a) an isolated polypeptide encoded by a polynucleotide comprising the sequence of SEQ ID NO:1;
(b) an isolated polypeptide comprising a polypeptide sequence having at least 95%, 96%, 97%, 98%, or 99% identity to the polypeptide sequence of SEQ ID NO:2;
(c) an isolated polypeptide comprising the polypeptide sequence of SEQ ID NO:2;
(d) an isolated polypeptide having at least 95%, 96%, 97%, 98%, or 99% identity to the polypeptide sequence of SEQ ID NO:2;
(e) the polypeptide sequence of SEQ ID NO:2; and
(f) an isolated polypeptide having or comprising a polypeptide sequence that has an Identity Index of 0.95, 0.96, 0.97, 0.98, or 0.99 compared to the polypeptide sequence of SEQ ID NO:2;
(g) fragments and variants of such polypeptides in (a) to (f).

Polypeptides of the present invention are believed to be members of the UDP-GalNac:polypeptide N-acetylgalactosaminyltransferase family of polypeptides. They are therefore of interest because O-linked sugars may help protect glycoproteins from proteolytic processing or add charge to the molecules to influence their ability to bind other matrix components. It is possible that the post-translational modification of glycoproteins and GAGs may be controlled by enzymes responsible for glycosylation of the protein core. Interestingly, bone sialoprotein levels have also been shown to change in patients with destructive joint disease (Lohmander, Baillere's, Clin. Rhem. 11I:711–726, 1997). Together, these studies indicate that glycosylation of cartilage matrix components could be key to control appropriate matrix integrity. These glycosylation patterns, controlled by specific glycosylation enzymes, change with joint pathology. Therefore, targeting these glycosylation enzymes could result in the development of compounds which may be effective in diseases where there is extensive matrix degradation. In addition, the pattern or levels of these enzymes may also be used as markers for disease diagnosis or prognosis. ppGaNTase-T6 is likely to function as a specific glycosylation enzyme in cartilage tissue and may play a role in pathology of osteoarthritis.

The biological properties of the ppGaNTase-T6 are hereinafter referred to as "biological activity of ppGaNTase-T6" or "ppGaNTase-T6 activity." Preferably, a polypeptide of the present invention exhibits at least one biological activity of ppGaNTase-T6.

Polypeptides of the present invention also include variants of the aforementioned polypeptides, including all allelic forms and splice variants. Such polypeptides vary from the reference polypeptide by insertions, deletions, and substitutions that may be conservative or non-conservative, or any combination thereof. Particularly preferred variants are those in which several, for instance from 50 to 30, from 30 to 20, from 20 to 10, from 10 to 5, from 5 to 3, from 3 to 2, from 2 to 1 or 1 amino acids are inserted, substituted, or deleted, in any combination.

Preferred fragments of polypeptides of the present invention include an isolated polypeptide comprising an amino acid sequence having at least 30, 50 or 100 contiguous amino acids from the amino acid sequence of SEQ ID NO: 2, or an isolated polypeptide comprising an amino acid sequence having at least 30, 50 or 100 contiguous amino acids truncated or deleted from the amino acid sequence of SEQ ID NO: 2. Preferred fragments are biologically active fragments that mediate the biological activity of ppGaNTase-T6, including those with a similar activity or an improved activity, or with a decreased undesirable activity. Also preferred are those fragments that are antigenic or immunogenic in an animal, especially in a human.

Fragments of the polypeptides of the invention may be employed for producing the corresponding full-length polypeptide by peptide synthesis; therefore, these variants may be employed as intermediates for producing the full-length polypeptides of the invention. The polypeptides of the present invention may be in the form of the "mature" protein or may be a part of a larger protein such as a precursor or a fusion protein. It is often advantageous to include an additional amino acid sequence that contains secretory or leader sequences, pro-sequences, sequences that aid in purification, for instance multiple histidine residues, or an additional sequence for stability during recombinant production.

Polypeptides of the present invention can be prepared in any suitable manner, for instance by isolation form naturally occurring sources, from genetically engineered host cells comprising expression systems (vide infra) or by chemical synthesis, using for instance automated peptide synthesizers, or a combination of such methods. Means for preparing such polypeptides are well understood in the art.

In a further aspect, the present invention relates to ppGaNTase-T6 polynucleotides. Such polynucleotides include:
(a) an isolated polynucleotide comprising a polynucleotide sequence having at least 95%, 96%, 97%, 98%, or 99% identity to the polynucleotide sequence of SEQ ID NO: 1;
(b) an isolated polynucleotide comprising the polynucleotide of SEQ ID NO: 1;
(c) an isolated polynucleotide having at least 95%, 96%, 97%, 98%, or 99% identity to the polynucleotide of SEQ ID NO:1;
(d) the isolated polynucleotide of SEQ ID NO: 1;
(e) an isolated polynucleotide comprising a polynucleotide sequence encoding a polypeptide sequence having at least 95%, 96%, 97%, 98%, or 99% identity to the polypeptide sequence of SEQ ID NO:2;
(f) an isolated polynucleotide comprising a polynucleotide sequence encoding the polypeptide of SEQ ID NO:2;
(g) an isolated polynucleotide having a polynucleotide sequence encoding a polypeptide sequence having at least 95%, 96%, 97%, 98%, or 99% identity to the polypeptide sequence of SEQ ID NO:2;
(h) an isolated polynucleotide encoding the polypeptide of SEQ ID NO:2;
(i) an isolated polynucleotide having or comprising a polynucleotide sequence that has an Identity Index of 0.95, 0.96, 0.97, 0.98, or 0.99 compared to the polynucleotide sequence of SEQ ID NO: 1;
j) an isolated polynucleotide having or comprising a polynucleotide sequence encoding a polypeptide sequence that has an Identity Index of 0.95, 0.96, 0.97, 0.98, or 0.99 compared to the polypeptide sequence of SEQ ID NO:2; and polynucleotides that are fragments and variants of the above mentioned polynucleotides or that are complementary to above mentioned polynucleotides, over the entire length thereof.

Preferred fragments of polynucleotides of the present invention include an isolated polynucleotide comprising an nucleotide sequence having at least 15, 30, 50 or 100 contiguous nucleotides from the sequence of SEQ ID NO: 1, or an isolated polynucleotide comprising an sequence having at least 30, 50 or 100 contiguous nucleotides truncated or deleted from the sequence of SEQ ID NO: 1.

Preferred variants of polynucleotides of the present invention include splice variants, allelic variants, and polymorphisms, including polynucleotides having one or more single nucleotide polymorphisms (SNPs).

Polynucleotides of the present invention also include polynucleotides encoding polypeptide variants that comprise the amino acid sequence of SEQ ID NO:2 and in which several, for instance from 50 to 30, from 30 to 20, from 20 to 10, from 10 to 5, from 5 to 3, from 3 to 2, from 2 to 1 or 1 amino acid residues are substituted, deleted or added, in any combination.

In a further aspect, the present invention provides polynucleotides that are RNA transcripts of the DNA sequences of the present invention. Accordingly, there is provided an RNA polynucleotide that:

(a) comprises an RNA transcript of the DNA sequence encoding the polypeptide of SEQ ID NO:2;

(b) is the RNA transcript of the DNA sequence encoding the polypeptide of SEQ ID NO:2;

(c) comprises an RNA transcript of the DNA sequence of SEQ ID NO: 1; or (d) is the RNA transcript of the DNA sequence of SEQ ID NO: 1;

and RNA polynucleotides that are complementary thereto. The polynucleotide sequence of SEQ ID NO:1 shows homology with human polynucleotide GalNAc transferase-T4 (ppGaNtase-T4, GenBank Accession # Y08564, Bennet et al. J. Biol. Chem. 273: 30472–30481, 1998) and with rat polynucleotide GalNAc transferase-T1 (ppGaNtase-T5, GenBank Accession # AF049344, Ten Hagen et al. J. Biol. Chem. 273: 27749–27754, 1998). The polynucleotide sequence of SEQ ID NO:1 is a cDNA sequence that encodes the polypeptide of SEQ ID NO:2. The polynucleotide sequence encoding the polypeptide of SEQ ID NO:2 may be identical to the polypeptide encoding sequence of SEQ ID NO:1 or it may be a sequence other than SEQ ID NO: 1, which, as a result of the redundancy (degeneracy) of the genetic code, also encodes the polypeptide of SEQ ID NO:2. The polypeptide of SEQ ID NO:2 is related to other proteins of the UDP-GalNac:polypeptide N-acetylgalactosaminyltransferase family, having homology and/or structural similarity with human polypeptide GalNAc transferase-T4 (ppGaNtase-T4, PID Accession # NP_003765, Bennet et al. J. Biol. Chem. 273: 30472–30481, 1998) and to human polypeptide GalNAc transferase-T3 (ppGaNtase-T3, PID Accession #NP_ 004473, Bennet et al. J. Biol. Chem. 271: 17006–17012, 1996).

Preferred polypeptides and polynucleotides of the present invention are expected to have, inter alia, similar biological functions/properties to their homologous polypeptides and polynucleotides. Furthermore, preferred polypeptides and polynucleotides of the present invention have at least one ppGaNTase-T6 activity.

Polynucleotides of the present invention may be obtained using standard cloning and screening techniques from a cDNA library derived from mRNA in cells of human osteoarthritic cartilage, (see for instance, Sambrook et al., Molecular Cloning: A Laboratory Manual, 2nd Ed., Cold Spring Harbor Laboratory Press, Cold Spring Harbor, N.Y. (1989)). Polynucleotides of the invention can also be obtained from natural sources such as genomic DNA libraries or can be synthesized using well known and commercially available techniques.

When polynucleotides of the present invention are used for the recombinant production of polypeptides of the present invention, the polynucleotide used may include the coding sequence for the mature polypeptide, by itself, or the coding sequence for the mature polypeptide in the reading frame with other coding sequences, such as those encoding a leader or secretory sequence, a pre-, or pro- or preproprotein sequence, or other fusion peptide portions. For example, a marker sequence that facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., Proc Natl Acad Sci USA (1989) 86:821–824, or is an HA tag. The polynucleotide may also contain non-coding 5' and 3' sequences, such as transcribed, non-translated sequences, splicing and polyadenylation signals, ribosome binding sites and sequences that stabilize mRNA.

Polynucleotides that are identical, or have sufficient identity to a polynucleotide sequence of SEQ ID NO:1, may be used as hybridization probes for cDNA and genomic DNA or as primers for a nucleic acid amplification reaction (for instance, PCR). Such probes and primers may be used to isolate full-length cDNAs and genomic clones encoding polypeptides of the present invention and to isolate cDNA and genomic clones of other genes (including genes encoding paralogs from human sources and orthologs and paralogs from species other than human) that have a high sequence similarity to SEQ ID NO:1, typically at least 95% identity. Preferred probes and primers will generally comprise at least 15 nucleotides, preferably, at least 30 nucleotides and may have at least 50, if not at least 100 nucleotides. Particularly preferred probes will have between 30 and 50 nucleotides. Particularly preferred primers will have between 20 and 25 nucleotides.

A polynucleotide encoding a polypeptide of the present invention, including homologs from species other than human, may be obtained by a process comprising the steps of screening a library under stringent hybridization conditions with a labeled probe having the sequence of SEQ ID NO: 1 or a fragment thereof, preferably of at least 15 nucleotides; and isolating full-length cDNA and genomic clones containing said polynucleotide sequence. Such hybridization techniques are well known to the skilled artisan. Preferred stringent hybridization conditions include overnight incubation at 420C in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 microgram/ml denatured, sheared salmon sperm DNA; followed by washing the filters in 0.1×SSC at about 65° C. Thus the present invention also includes isolated polynucleotides, preferably with a nucleotide sequence of at least 100, obtained by screening a library under stringent hybridization conditions with a labeled probe having the sequence of SEQ ID NO:1 or a fragment thereof, preferably of at least 15 nucleotides.

The skilled artisan will appreciate that, in many cases, an isolated cDNA sequence will be incomplete, in that the region coding for the polypeptide does not extend all the way through to the 5' terminus. This is a consequence of reverse transcriptase, an enzyme with inherently low "processivity" (a measure of the ability of the enzyme to remain attached to the template during the polymerization reaction), failing to complete a DNA copy of the mRNA template during first strand cDNA synthesis.

There are several methods available and well known to those skilled in the art to obtain full-length cDNAs, or extend short cDNAs, for example those based on the method of Rapid Amplification of cDNA ends (RACE) (see, for example, Frohman et al., Proc Nat Acad Sci USA 85, 8998–9002, 1988). Recent modifications of the technique, exemplified by the Marathon (trade mark) technology (Clontech Laboratories Inc.) for example, have significantly simplified the search for longer cDNAs. In the Marathon (trade mark) technology, cDNAs have been prepared from mRNA extracted from a chosen tissue and an 'adaptor' sequence ligated onto each end. Nucleic acid amplification (PCR) is then carried out to amplify the "missing" 5' end of the cDNA using a combination of gene specific and adaptor specific oligonucleotide primers. The PCR reaction is then repeated using 'nested' primers, that is, primers designed to anneal within the amplified product (typically an adaptor specific primer that anneals further 3' in the adaptor sequence and a gene specific primer that anneals further 5' in the known gene sequence). The products of this reaction can then be analyzed by DNA sequencing and a full-length cDNA constructed either by joining the product directly to the existing cDNA to give a complete sequence, or carrying out a separate full-length PCR using the new sequence information for the design of the 5' primer.

The recombinant polypeptides of the present invention may be prepared by processes well known in the art. In one such example, the polypeptides are prepared by genetically engineered host cells comprising expression systems. Accordingly, in a further aspect, the present invention relates to expression systems comprising a polynucleotide or polynucleotides of the present invention, to host cells which are genetically engineered with such expression systems and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Polynucleotides may be introduced into host cells by methods described in many standard laboratory manuals, such as Davis et al., Basic Methods in Molecular Biology (1986) and Sambrook et al.(ibid). Preferred methods of introducing polynucleotides into host cells include, for instance, calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as Streptococci, Staphylococci, *E. coli*, Streptomyces and *Bacillus subtilis* cells; fungal cells, such as yeast cells and Aspergillus cells; insect cells such as Drosophila S2 and Spodoptera Sf9 cells; animal cells such as CHO, COS, HeLa, C127, 3T3, BHK, HEK 293 and Bowes melanoma cells; and plant cells.

A great variety of expression systems can be used, for instance, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector that is able to maintain, propagate or express a polynucleotide to produce a polypeptide in a host may be used. The appropriate polynucleotide sequence may be inserted into an expression system by any of a variety of well-known and routine techniques, such as, for example, those set forth in Sambrook et al., (ibid). Appropriate secretion signals may be incorporated into the desired polypeptide to allow secretion of the translated protein into the lumen of the endoplasmic reticulum, the periplasmic space or the extracellular environment. These signals may be endogenous to the polypeptide or they may be heterologous signals.

If a polypeptide of the present invention is to be expressed for use in screening assays, it is generally preferred that the polypeptide be produced at the surface of the cell. In this event, the cells may be harvested prior to use in the screening assay. If the polypeptide is secreted into the medium, the medium can be recovered in order to recover and purify the polypeptide. If produced intracellularly, the cells must first be lysed before the polypeptide is recovered.

Polypeptides of the present invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during intracellular synthesis, isolation and/or purification.

Polynucleotides of the present invention may be used as diagnostic reagents, through detecting mutations in the associated gene. Detection of a mutated form of the gene characterized by the polynucleotide of SEQ ID NO:1 in the cDNA or genomic sequence and which is associated with a dysfunction will provide a diagnostic tool that can add to, or define, a diagnosis of a disease, or susceptibility to a disease, which results from under-expression, over-expression or altered spatial or temporal expression of the gene. Individuals carrying mutations in the gene may be detected at the DNA level by a variety of techniques well known in the art.

Nucleic acids for diagnosis may be obtained from a subject's cells, such as from blood, urine, saliva, tissue biopsy or autopsy material. The genomic DNA may be used directly for detection or it may be amplified enzymatically by using PCR, preferably RT-PCR, or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled ppGaNTase-T6 nucleotide sequences. Perfectly matched sequences can be distinguished from mismatched duplexes by RNase digestion or by differences in melting temperatures. DNA sequence difference may also be detected by alterations in the electrophoretic mobility of DNA fragments in gels, with or without denaturing agents, or by direct DNA sequencing (see, for instance, Myers et al., Science (1985) 230:1242). Sequence changes at specific locations may also be revealed by nuclease protection assays, such as RNase and S1 protection or the chemical cleavage method (see Cotton et al., Proc Natl Acad Sci USA (1985) 85: 4397–4401).

An array of oligonucleotides probes comprising ppGaNTase-T6 polynucleotide sequence or fragments thereof can be constructed to conduct efficient screening of e.g., genetic mutations. Such arrays are preferably high density arrays or grids. Array technology methods are well known and have general applicability and can be used to address a variety of questions in molecular genetics including gene expression, genetic linkage, and genetic variability, see, for example, M. Chee et al., Science, 274, 610–613 (1996) and other references cited therein.

Detection of abnormally decreased or increased levels of polypeptide or mRNA expression may also be used for diagnosing or determining susceptibility of a subject to a disease of the invention. Decreased or increased expression can be measured at the RNA level using any of the methods well known in the art for the quantification of polynucleotides, such as, for example, nucleic acid amplification, for instance PCR, RT-PCR, RNase protection, Northern blotting and other hybridization methods. Assay techniques that can be used to determine levels of a protein, such as a polypeptide of the present invention, in a sample derived from a host are well-known to those of skill in the art. Such assay methods include radioimmunoassays, competitive-binding assays, Western Blot analysis and ELISA assays.

Thus in another aspect, the present invention relates to a diagnostic kit comprising:
(a) a polynucleotide of the present invention, preferably the nucleotide sequence of SEQ ID NO: 1, or a fragment or an RNA transcript thereof,
(b) a nucleotide sequence complementary to that of (a);
(c) a polypeptide of the present invention, preferably the polypeptide of SEQ ID NO:2 or a fragment thereof; or
(d) an antibody to a polypeptide of the present invention, preferably to the polypeptide of SEQ ID NO:2.

It will be appreciated that in any such kit, (a), (b), (c) or (d) may comprise a substantial component. Such a kit will be of use in diagnosing a disease or susceptibility to a disease, particularly diseases of the invention, amongst others.

The polynucleotide sequences of the present invention are valuable for chromosome localization studies. The sequence is specifically targeted to, and can hybridize with, a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found in, for example, V. McKusick, Mendelian Inheritance in Man (available on-line through Johns Hopkins University Welch Medical Library). The relationship between genes and diseases that have been mapped to the same chromosomal region are then identified through linkage analysis (co-inheritance of physically adjacent genes). Precise human chromosomal localization for a genomic sequence (gene fragment etc.) can be determined using Radiation Hybrid (RH) Mapping (Walter, M. Spillett, D., Thomas, P., Weissenbach, J., and Goodfellow, P., (1994) A method for constructing radiation hybrid maps of whole genomes, Nature Genetics 7, 22–28). A number of RH panels are available from Research Genetics (Huntsville, Ala., USA) e.g. the GeneBridge4 RH panel (Hum Mol Genet 1996 Mar;5(3):339–46 A radiation hybrid map of the human genome. Gyapay G, Schmitt K, Fizames C, Jones H, Vega-Czarny N, Spillett D, Muselet D, Prud'Homme J F, Dib C, Auffray C, Morissette J, Weissenbach J, Goodfellow P N). To determine the chromosomal location of a gene using this panel, 93 PCRs are performed using primers designed from the gene of interest on RH DNAs. Each of these DNAs contains random human genomic fragments maintained in a hamster background (human/hamster hybrid cell lines). These PCRs result in 93 scores indicating the presence or absence of the PCR product of the gene of interest. These scores are compared with scores created using PCR products from genomic sequences of known location. This comparison is conducted at http://www.genome.wi.mit.edu.

The polynucleotide sequences of the present invention are also valuable tools for tissue expression studies. Such studies allow the determination of expression patterns of polynucleotides of the present invention that may give an indication as to the expression patterns of the encoded polypeptides in tissues, by detecting the mRNAs that encode them. The techniques used are well known in the art and include in situ hybridization techniques to clones arrayed on a grid, such as cDNA microarray hybridization (Schena et al, Science, 270, 467–470, 1995 and Shalon et al, Genome Res, 6, 639–645, 1996) and nucleotide amplification techniques such as PCR. A preferred method uses the TAQMAN (Trade mark) technology available from Perkin Elmer. Results from these studies can provide an indication of the normal function of the polypeptide in the organism. In addition, comparative studies of the normal expression pattern of mRNAs with that of mRNAs encoded by an alternative form of the same gene (for example, one having an alteration in polypeptide coding potential or a regulatory mutation) can provide valuable insights into the role of the polypeptides of the present invention, or that of inappropriate expression thereof in disease. Such inappropriate expression may be of a temporal, spatial or simply quantitative nature.

The polypeptides of the present invention are expressed in normal and osteoarthritic human cartilage.

A further aspect of the present invention relates to antibodies. The polypeptides of the invention or their fragments, or cells expressing them, can be used as immunogens to produce antibodies that are immunospecific for polypeptides of the present invention. The term "immunospecific" means that the antibodies have substantially greater affinity for the polypeptides of the invention than their affinity for other related polypeptides in the prior art.

Antibodies generated against polypeptides of the present invention may be obtained by administering the polypeptides or epitope-bearing fragments, or cells to an animal, preferably a non-human animal, using routine protocols. For preparation of monoclonal antibodies, any technique that provides antibodies produced by continuous cell line cultures can be used. Examples include the hybridoma technique (Kohler, G. and Milstein, C., Nature (1975) 256:495–497), the trioma technique, the human B-cell hybridoma technique (Kozbor et al., Immunology Today (1983) 4:72) and the EBV-hybridoma technique (Cole et al., Monoclonal Antibodies and Cancer Therapy, 77–96, Alan R. Liss, Inc., 1985).

Techniques for the production of single chain antibodies, such as those described in U.S. Pat. No. 4,946,778, can also be adapted to produce single chain antibodies to polypeptides of this invention. Also, transgenic mice, or other organisms, including other mammals, may be used to express humanized antibodies.

The above-described antibodies may be employed to isolate or to identify clones expressing the polypeptide or to purify the polypeptides by affinity chromatography. Antibodies against polypeptides of the present invention may also be employed to treat diseases of the invention, amongst others.

Polypeptides and polynucleotides of the present invention may also be used as vaccines. Accordingly, in a further aspect, the present invention relates to a method for inducing an immunological response in a mammal that comprises inoculating the mammal with a polypeptide of the present invention, adequate to produce antibody and/or T cell immune response, including, for example, cytokine-producing T cells or cytotoxic T cells, to protect said animal from disease, whether that disease is already established within the individual or not. An immunological response in a mammal may also be induced by a method comprising delivering a polypeptide of the present invention via a vector directing expression of the polynucleotide and coding for the polypeptide in vivo in order to induce such an immunological response to produce an antibody to protect said animal from diseases of the invention.

One way of administering the vector is by accelerating it into the desired cells as a coating on particles or otherwise. Such nucleic acid vector may comprise DNA, RNA, a modified nucleic acid, or a DNA/RNA hybrid. For use a vaccine, a polypeptide or a nucleic acid vector will be normally provided as a vaccine formulation (composition). The formulation may further comprise a suitable carrier. Since a polypeptide may be broken down in the stomach, it is preferably administered parenterally (for instance, subcutaneous, intramuscular, intravenous, or intradermal injection). Formulations suitable for parenteral administration include aqueous and non-aqueous sterile injection solutions that may contain anti-oxidants, buffers, bacteriostats and solutes that render the formulation isotonic with the blood of the recipient; and aqueous and non-aqueous sterile suspensions that may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Polypeptides of the present invention have one or more biological functions that are of relevance in one or more disease states, in particular the diseases of the invention mentioned above. It is therefore useful to identify compounds that stimulate or inhibit the function or level of the polypeptide. Accordingly, in a further aspect, the present invention provides for a method of screening compounds to identify those that stimulate or inhibit the function or level of the polypeptide. Such methods identify agonists or antagonists that may be employed for therapeutic and prophylactic purposes for such diseases of the invention as mentioned herein. Compounds may be identified from a variety of sources, for example, cells, cell-free preparations, chemical libraries, collections of chemical compounds, and natural product mixtures. Such agonists or antagonists so-identified may be natural or modified substrates, ligands, receptors, enzymes, etc., as the case may be, of the polypeptide; a structural or functional mimetic thereof (see Coligan et aL, Current Protocols in Immunology 1(2):Chapter 5 (1991)) or a small molecule. Such small molecules preferably have a molecular weight below 2,000 daltons, more preferably between 300 and 1,000 daltons, and most preferably between 400 and 700 daltons. It is preferred that these small molecules are organic molecules.

The screening method may simply measure the binding of a candidate compound to the polypeptide, or to cells or membranes bearing the polypeptide, or a fusion protein thereof, by means of a label directly or indirectly associated with the candidate compound. Alternatively, the screening method may involve measuring or detecting (qualitatively or quantitatively) the competitive binding of a candidate compound to the polypeptide against a labeled competitor (e.g. agonist or antagonist). Further, these screening methods may test whether the candidate compound results in a signal generated by activation or inhibition of the polypeptide, using detection systems appropriate to the cells bearing the polypeptide. Inhibitors of activation are generally assayed in the presence of a known agonist and the effect on activation by the agonist by the presence of the candidate compound is observed. Further, the screening methods may simply comprise the steps of mixing a candidate compound with a solution containing a polypeptide of the present invention, to form a mixture, measuring a ppGaNTase-T6 activity in the mixture, and comparing the ppGaNTase-T6 activity of the mixture to a control mixture which contains no candidate compound.

Polypeptides of the present invention may be employed in conventional low capacity screening methods and also in high-throughput screening (HTS) formats. Such HTS formats include not only the well-established use of 96- and, more recently, 384-well micotiter plates but also emerging methods such as the nanowell method described by Schullek et al, Anal Biochem., 246, 20–29, (1997).

Fusion proteins, such as those made from Fc portion and ppGaNTase-T6 polypeptide, as hereinbefore described, can also be used for high-throughput screening assays to identify antagonists for the polypeptide of the present invention (see D. Bennett et al., J Mol Recognition, 8:52–58 (1995); and K. Johanson et al., J Biol Chem, 270(16):9459–9471 (1995)).

The polynucleotides, polypeptides and antibodies to the polypeptide of the present invention may also be used to configure screening methods for detecting the effect of added compounds on the production of mRNA and polypeptide in cells. For example, an ELISA assay may be constructed for measuring secreted or cell associated levels of polypeptide using monoclonal and polyclonal antibodies by standard methods known in the art. This can be used to discover agents that may inhibit or enhance the production of polypeptide (also called antagonist or agonist, respectively) from suitably manipulated cells or tissues.

A polypeptide of the present invention may be used to identify membrane bound or soluble receptors, if any, through standard receptor binding techniques known in the art. These include, but are not limited to, ligand binding and crosslinking assays in which the polypeptide is labeled with a radioactive isotope (for instance, $^{125}$I), chemically modified (for instance, biotinylated), or fused to a peptide sequence suitable for detection or purification, and incubated with a source of the putative receptor (cells, cell membranes, cell supernatants, tissue extracts, bodily fluids). Other methods include biophysical techniques such as surface plasmon resonance and spectroscopy. These screening methods may also be used to identify agonists and antagonists of the polypeptide that compete with the binding of the polypeptide to its receptors, if any. Standard methods for conducting such assays are well understood in the art.

Examples of antagonists of polypeptides of the present invention include antibodies or, in some cases, oligonucleotides or proteins that are closely related to the ligands, substrates, receptors, enzymes, etc., as the case may be, of the polypeptide, e.g., a fragment of the ligands, substrates, receptors, enzymes, etc.; or a small molecule that bind to the polypeptide of the present invention but do not elicit a response, so that the activity of the polypeptide is prevented.

Screening methods may also involve the use of transgenic technology and ppGaNTase-T6 gene.

The art of constructing transgenic animals is well established. For example, the ppGaNTase-T6 gene may be introduced through microinjection into the male pronucleus of fertilized oocytes, retroviral transfer into pre- or post-implantation embryos, or injection of genetically modified, such as by electroporation, embryonic stem cells into host blastocysts. Particularly useful transgenic animals are so-called "knock-in" animals in which an animal gene is replaced by the human equivalent within the genome of that animal. Knock-in transgenic animals are useful in the drug discovery process, for target validation, where the compound is specific for the human target. Other useful transgenic animals are so-called "knock-out" animals in which the expression of the animal ortholog of a polypeptide of the present invention and encoded by an endogenous DNA sequence in a cell is partially or completely annulled. The gene knock-out may be targeted to specific cells or tissues, may occur only in certain cells or tissues as a consequence of the limitations of the technology, or may occur in all, or substantially all, cells in the animal. Transgenic animal technology also offers a whole animal expression-cloning system in which introduced genes are expressed to give large amounts of polypeptides of the present invention Screening kits for use in the above described methods form a further aspect of the present —invention. Such screening kits comprise:

(a) a polypeptide of the present invention;
(b) a recombinant cell expressing a polypeptide of the present invention;
(c) a cell membrane expressing a polypeptide of the present invention; or
(d) an antibody to a polypeptide of the present invention;

which polypeptide is preferably that of SEQ ID NO:2.

It will be appreciated that in any such kit, (a), (b), (c) or (d) may comprise a substantial component.

Glossary

The following definitions are provided to facilitate understanding of certain terms used frequently hereinbefore.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein. Moreover, a polynucleotide or polypeptide that is introduced into an organism by transformation, genetic manipulation or by any other recombinant method is "isolated" even if it is still present in said organism, which organism may be living or non-living.

"Polynucleotide" generally refers to any polyribonucleotide (RNA) or polydeoxribonucleotide (DNA), which may be unmodified or modified RNA or DNA. "Polynucleotides" include, without limitation, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term "polynucleotide" also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any polypeptide comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques that are well known in the art. Such modifications are well-described in basic texts and in more detailed monographs, as well as in a voluminous research literature. Modifications may occur anywhere in a polypeptide, including the peptide backbone, the amino acid side-chains and the amino or carboxyl termini. It will be appreciated that the same type of modification may be present to the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from post-translation natural processes or may be made by synthetic methods. Modifications include acetylation, acylation, ADP-ribosylation, amidation, biotinylation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination (see, for instance, Proteins—Structure and Molecular Properties, 2nd Ed., T. E. Creighton, W. H. Freeman and Company, New York, 1993; Wold, F., Post-translational Protein Modifications: Perspectives and Prospects, 1-12, in Post-translational Covalent Modification of Proteins, B. C. Johnson, Ed., Academic Press, New York, 1983; Seifter et al., "Analysis for protein modifications and nonprotein cofactors", Meth Enzymol, 182, 626–646, 1990, and Rattan et al., "Protein Synthesis: Post-translational Modifications and Aging", Ann NY Acad Sci, 663, 48–62, 1992).

"Fragment" of a polypeptide sequence refers to a polypeptide sequence that is shorter than the reference sequence but that retains essentially the same biological function or activity as the reference polypeptide. "Fragment" of a polynucleotide sequence refers to a polynucleotide sequence that is shorter than the reference sequence of SEQ ID NO:1.

"Variant" refers to a polynucleotide or polypeptide that differs from a reference polynucleotide or polypeptide, but retains the essential properties thereof. A typical variant of a polynucleotide differs in nucleotide sequence from the reference polynucleotide. Changes in the nucleotide sequence of the variant may or may not alter the amino acid sequence of a polypeptide encoded by the reference polynucleotide.

Nucleotide changes may result in amino acid substitutions, additions, deletions, fusions and truncations in the polypeptide encoded by the reference sequence, as discussed below. A typical variant of a polypeptide differs in amino acid sequence from the reference polypeptide. Generally, alterations are limited so that the sequences of the reference polypeptide and the variant are closely similar overall and, in many regions, identical. A variant and reference polypeptide may differ in amino acid sequence by one or more substitutions, insertions, deletions in any combination. A substituted or inserted amino acid residue may or may not be one encoded by the genetic code. Typical conservative substitutions include Gly, Ala; Val, Ile, Leu; Asp, Glu; Asn, Gln; Ser, Thr; Lys, Arg; and Phe and Tyr. A variant of a polynucleotide or polypeptide may be naturally occurring such as an allele, or it may be a variant that is not known to occur naturally. Non-naturally occurring variants of polynucleotides and polypeptides may be made by mutagenesis techniques or by direct synthesis. Also included as variants are polypeptides having one or more post-translational modifications, for instance glycosylation, phosphorylation, methylation, ADP ribosylation and the like. Embodiments include methylation of the N-terminal amino acid, phosphorylations of serines and threonines and modification of C-terminal glycines.

"Allele" refers to one of two or more alternative forms of a gene occurring at a given locus in the genome.

"Polymorphism" refers to a variation in nucleotide sequence (and encoded polypeptide sequence, if relevant) at a given position in the genome within a population.

"Single Nucleotide Polymorphism" (SNP) refers to the occurrence of nucleotide variability at a single nucleotide position in the genome, within a population. An SNP may occur within a gene or within intergenic regions of the genome. SNPs can be assayed using Allele Specific Amplification (ASA). For the process at least 3 primers are required. A common primer is used in reverse complement to the polymorphism being assayed. This common primer can be between 50 and 1500 bps from the polymorphic base. The other two (or more) primers are identical to each other except that the final 3' base wobbles to match one of the two (or more) alleles that make up the polymorphism. Two (or more) PCR reactions are then conducted on sample DNA, each using the common primer and one of the Allele Specific Primers.

"Splice Variant" as used herein refers to cDNA molecules produced from RNA molecules initially transcribed from the same genomic DNA sequence but which have undergone alternative RNA splicing. Alternative RNA splicing occurs when a primary RNA transcript undergoes splicing, generally for the removal of introns, which results in the production of more than one mRNA molecule each of that may encode different amino acid sequences. The term splice variant also refers to the proteins encoded by the above cDNA molecules.

"Identity" reflects a relationship between two or more polypeptide sequences or two or more polynucleotide sequences, determined by comparing the sequences. In general, identity refers to an exact nucleotide to nucleotide or amino acid to amino acid correspondence of the two polynucleotide or two polypeptide sequences, respectively, over the length of the sequences being compared.

"% Identity"—For sequences where there is not an exact correspondence, a "% identity" may be determined. In general, the two sequences to be compared are aligned to give a maximum correlation between the sequences. This may include inserting "gaps" in either one or both sequences, to enhance the degree of alignment. A % identity may be determined over the whole length of each of the sequences being compared (so-called global alignment), that is particularly suitable for sequences of the same or very similar length, or over shorter, defined lengths (so-called local alignment), that is more suitable for sequences of unequal length.

"Similarity" is a further, more sophisticated measure of the relationship between two polypeptide sequences. In general, "similarity" means a comparison between the amino acids of two polypeptide chains, on a residue by residue basis, taking into account not only exact correspondences between a between pairs of residues, one from each of the sequences being compared (as for identity) but also, where there is not an exact correspondence, whether, on an evolutionary basis, one residue is a likely substitute for the other. This likelihood has an associated "score" from which the "% similarity" of the two sequences can then be determined.

Methods for comparing the identity and similarity of two or more sequences are well known in the art. Thus for instance, programs available in the Wisconsin Sequence Analysis Package, version 9.1 (Devereux J et al, Nucleic Acids Res, 12, 387–395, 1984, available from Genetics Computer Group, Madison, Wis., USA), for example the programs BESTFIT and GAP, may be used to determine the % identity between two polynucleotides and the % identity and the % similarity between two polypeptide sequences. BESTFIT uses the "local homology" algorithm of Smith and Waterman (3 Mol Biol, 147,195–197, 1981, Advances in Applied Mathematics, 2, 482–489, 1981) and finds the best single region of similarity between two sequences. BESTFIT is more suited to comparing two polynucleotide or two polypeptide sequences that are dissimilar in length, the program assuming that the shorter sequence represents a portion of the longer. In comparison, GAP aligns two sequences, finding a "maximum similarity", according to the algorithm of Neddleman and Wunsch (J Mol Biol, 48, 443–453, 1970). GAP is more suited to comparing sequences that are approximately the same length and an alignment is expected over the entire length. Preferably, the parameters "Gap Weight" and "Length Weight" used in each program are 50 and 3, for polynucleotide sequences and 12 and 4 for polypeptide sequences, respectively. Preferably, % identities and similarities are determined when the two sequences being compared are optimally aligned.

Other programs for determining identity and/or similarity between sequences are also known in the art, for instance the BLAST family of programs (Altschul S F et al, J Mol Biol, 215, 403–410, 1990, Altschul S F et al, Nucleic Acids Res., 25:389–3402, 1997, available from the National Center for Biotechnology Information (NCBI), Bethesda, Md., USA and accessible through the home page of the NCBI at www.ncbi.nlm.nih.gov) and FASTA (Pearson W R, Methods in Enzymology, 183, 63–99, 1990; Pearson W R and Lipman D J, Proc Nat Acad Sci USA, 85, 2444–2448,1988, available as part of the Wisconsin Sequence Analysis Package).

Preferably, the BLOSUM62 amino acid substitution matrix (Henikoff S and Henikoff J G, Proc. 715 Nat. Acad Sci. USA, 89, 10915–10919, 1992) is used in polypeptide sequence comparisons including where nucleotide sequences are first translated into amino acid sequences before comparison.

Preferably, the program BESTFIT is used to determine the % identity of a query polynucleotide or a polypeptide sequence with respect to a reference polynucleotide or a polypeptide sequence, the query and the reference sequence being optimally aligned and the parameters of the program set at the default value, as hereinbefore described.

"Identity Index" is a measure of sequence relatedness that may be used to compare a candidate sequence (polynucleotide or polypeptide) and a reference sequence. Thus, for instance, a candidate polynucleotide sequence having, for example, an Identity Index of 0.95 compared to a reference polynucleotide sequence is identical to the reference sequence except that the candidate polynucleotide sequence may include on average up to five differences per each 100 nucleotides of the reference sequence. Such differences are selected from the group consisting of at least one nucleotide deletion, substitution, including transition and transversion, or insertion. These differences may occur at the 5' or 3' terminal positions of the reference polynucleotide sequence or anywhere between these terminal positions, interspersed either individually among the nucleotides in the reference sequence or in one or more contiguous groups within the reference sequence. In other words, to obtain a polynucleotide sequence having an Identity Index of 0.95 compared to a reference polynucleotide sequence, an average of up to 5 in every 100 of the nucleotides of the in the reference sequence may be deleted, substituted or inserted, or any combination thereof, as hereinbefore described. The same applies mutatis mutandis for other values of the Identity Index, for instance 0.96, 0.97, 0.98 and 0.99.

Similarly, for a polypeptide, a candidate polypeptide sequence having, for example, an Identity Index of 0.95 compared to a reference polypeptide sequence is identical to the reference sequence except that the polypeptide sequence may include an average of up to five differences per each 100 amino acids of the reference sequence. Such differences are selected from the group consisting of at least one amino acid deletion, substitution, including conservative and non-conservative substitution, or insertion. These differences may occur at the amino- or carboxy-terminal positions of the reference polypeptide sequence or anywhere between these terminal positions, interspersed either individually among the amino acids in the reference sequence or in one or more contiguous groups within the reference sequence. In other words, to obtain a polypeptide sequence having an Identity Index of 0.95 compared to a reference polypeptide sequence, an average of up to 5 in every 100 of the amino acids in the reference sequence may be deleted, substituted or inserted, or any combination thereof, as hereinbefore described. The same applies mutatis mutandis for other values of the Identity Index, for instance 0.96, 0.97, 0.98 and 0.99.

The relationship between the number of nucleotide or amino acid differences and the Identity Index may be expressed in the following equation:

$$n_a \leq x_a - (x_a \cdot I)$$

in which:

$n_a$ is the number of nucleotide or amino acid differences, $x_a$ is the total number of nucleotides or amino acids in SEQ ID NO:1 or SEQ ID NO:2, respectively, I is the Identity Index, · is the symbol for the multiplication operator, and in which any non-integer product of $x_a$ and I is rounded down to the nearest integer prior to subtracting it from $x_a$.

"Homolog" is a generic term used in the art to indicate a polynucleotide or polypeptide sequence possessing a high degree of sequence relatedness to a reference sequence. Such relatedness may be quantified by determining the degree of identity and/or similarity between the two sequences as hereinbefore defined. Falling within this generic term are the terms "ortholog", and "paralog". "Ortholog" refers to a polynucleotide or polypeptide that is the functional equivalent of the polynucleotide or polypeptide in another species. "Paralog" refers to a polynucleotide or polypeptide that within the same species which is functionally similar.

"Fusion protein" refers to a protein encoded by two, often unrelated, fused genes or fragments thereof. In one example, EP-A-0 464 533-A discloses fusion proteins comprising various portions of constant region of immunoglobulin molecules together with another human protein or part thereof. In many cases, employing an immunoglobulin Fc region as a part of a fusion protein is advantageous for use in therapy and diagnosis resulting in, for example, improved pharmacokinetic properties [see, e.g., EP-A 0232 262]. On the other hand, for some uses it would be desirable to be able to delete the Fc part after the fusion protein has been expressed, detected and purified.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

EXAMPLE 1

Cloning of ppGaNTase-T6 Full Length cDNA:

An assembly containing 9 ESTs from human osteoarthritic cartilage cDNA library was chosen for analysis as it represented a completely unknown gene. One of the ESTs, HOA 12F 10, from this assembly was fully sequenced. The full length sequence contained 3357 nucleotides with a single open reading frame of 1917 nucleotides encoding a polypeptide of 639 amino acids. The predicted protein appears to be a novel homologue of UDP-GalNac:polypeptide N-acetylgalactosaminyltransferases (ppGaNTase, EC 2.4.1.41) family of sugar transferring enzyme and hence it was termed ppGaNTase-T6. Sequence analysis suggests that ppGaNTase-T6 contains an N-terminal 13-amino acid (aa) cytoplasmic tail, followed by a 20-aa hydrophobic sequence (as predicted by the algorithm of von Heijne, Eur. J. Bioch. 133:17–21, 1983), followed by a 125-aa stem region and a 481 aa catalytic domain that has extensive homology to various ppGaNTases. Like other members of this family, ppGaNTase-T6 is likely to be a type II transmembrane protein with its catalytic domain in Golgi apparatus and N-terminus tail in the cytoplasm.

A database search revealed several ESTs with homology to various regions of ppGaNTase-T6. The majority of these ESTs come from human osteoarthritic cartilage suggesting that the ppGaNTase-T6 is highly expressed in this tissue. Few ESTs were also identified from a public GenBank database search. These ESTs were from placenta, fetal heart, testes and libraries of mixed tissues (melanocyte, pregnant uterus and fetal heart; lung, testes and B-cells).

EXAMPLE 2

Tissue Distribution:

Two multiple tissue Northern blots (prepared using 24 human tissues and cell lines) were screened using a ppGaNTase-T6 cDNA probe using a standard procedure (Sambrook et al., Molecular Cloning: a laboratory manual, 2nd Ed. Cold Spring Harbor Lab Press, NY (1989). The expression of a single ~4.5 Kb MRNA was detected only in the normal and osteoarthritic cartilage and osteosarcoma Saos2 cells.

SEQUENCE INFORMATION

SEQ ID NO:1

ATGCTCCTAAGGAAGCGATACAGGCACAGACCATGCAGACTCCAGTTCCTCCTGCTGCTCCTGATGCTGGGATGCGTCCT

GATGATGGTGGCGATGTTGCACCCTCCCCACCACACCCTGCACCAGACTGTCACAGCCCAAGCCAGCAAGCACAGCCCTG

AAGCCAGGTACCGCCTGGACTTTGGGGAATCCCAGGATTGGGTACTGGAAGCTGAGGATGAGGGTGAAGAGTACAGCCCT

CTGGAGGGCCTGCCACCCTTTATCTCACTGCGGGAGGATCAGCTGCTGGTGGCCGTGGCCTTACCCCAGGCCAGAAGGAA

CCAGAGCCAGGGCAGGAGAGGTGGGAGCTACCGCCTCATCAAGCAGCCAAGGAGGCAGGATAAGGAAGCCCCAAAGAGGG

ACTGGGGGGCTGATGAGGACGGGGAGGTGTCTGAAGAAGAGGAGTTGACCCCGTTCAGCCTGGACCCACGTGGCCTCCAG

GAGGCACTCAGTGCCCGCATCCCCCTCCAGAGGGCTCTGCCCGAGGTGCGGCACCCACTGTGTCTGCAGCAGCACCCTCA

GGACAGCCTGCCCACAGCCAGCGTCATCCTCTGTTTCCATGATGAGGCCTGGTCCACTCTCCTGCGGACTGTACACAGCA

TCCTCGACACAGTGCCCAGGGCCTTCCTGAAGGAGATCATCCTCGTGGACGACCTCAGCCAGCAAGGACAACTCAAGTCT

GCTCTCAGCGAATATGTGGCCAGGCTGGAGGGGTGAAGTTACTCAGGAGCAACAAGAGGCTGGGTGCCATCAGGGCCCG

GATGCTGGGGCCACCAGAGCCACCGGGGATGTGCTCGTCTTCATGGATGCCCACTGCGAGTGCCACCCAGGCTGGCTGG

AGCCCCTCCTCAGCAGAATAGCTGGTGACAGGAGCCGAGTGGTATCTCCGGTGATAGATGTGATTGACTGGAAGACTTTC

CAGTATTACCCCTCAAAGGACCTGCAGCGTGGGGTGTTGGACTGGAAGCTGGATTTCCACTGGGAACCTTTGCCAGAGCA

TGTGAGGAAGGCCCTCCAGTCCCCCATAAGCCCCATCAGGAGCCCTGTGGTGCCGGAGAGGTGGTGGCCATGGACAGAC

ATTACTTCCAAAACACTGGAGCGTATGACTCTCTTATGTCGCTGCGAGGTGGTGAAAACCTCGAACTGTCTTTCAAGGCC

TGGCTCTGTGGTGGCTCTGTTGAAATCCTTCCCTGCTCTCGGGTAGGACACATCTACCAAAATCAGGATTCCCATTCCCC

CCTCGACCAGGAGGCCACCCTGAGGAACAGGGTTCGCATTGCTGAGACCTGGCTGGGGTCATTCAAAGAAACCTTCTACA

AGCATAGCCCAGAGGCCTTCTCCTTGAGCAAGGCTGAGAAGCCAGACTGCATGGAACGCTTGCAGCTGCAAAGGAGACTG

GGTTGTCGGACATTCCACTGGTTTCTGGCTAATGTCTACCCTGAGCTGTACCCATCTGAACCCAGGCCCAGTTTCTCTGG

AAAGCTCCACAACACTGGACTTGGGCTCTGTGCAGACTGCCAGGCAGAAGGGACATCCTGGGCTGTCCCATGGTGTTGG

CTCCTTGCAGTGACAGCCGGCAGCAACAGTACCTGCAGCACACCAGCAGGAAGGAGATTCACTTTGGCAGCCCACAGCAC

CTGTGCTTTGCTGTCAGGCAGGAGCAGGTGATTCTTCAGAACTGCACGGAGGAAGGCCTGGCCATCCACCAGCAGCACTG

GGACTTCCAGGAGAATGGGATGATTGTCCACATTCTTTCTGGGAAATGCATGGAAGCTGTGGTGCAAGAAAACAATAAAG

ATTTGTACCTGCGTCCGTGTGATGGAAAAGCCCGCCAGCAGTGGCGTTTTGACCAGATCAATGCTGTGGATGAACGATGA

SEQ ID NO:2

MLLRKRYRHRPCRLQFLLLLLMLGCVLMMVAMLHPPHHTLHQTVTAQASKHSPEARYRLDFGESQDWVLEAEDEGEEYSP

LEGLPPFISLREDQLLVAVALPQARRNQSQGRRGGSYRLIKQPRRQDKEAPKRDWGADEDGEVSEEEELTPFSLDPRGLQ

EALSARIPLQRALPEVRHPLCLQQHPQDSLPTASVILCFHDEAWSTLLRTVHSILDTVPRAFLKEIILVDDLSQQGQLKS

ALSEYVARLEGVKLLRSNKRLGAIRARMLGATRATGDVLVFMDAHCECHPGWLEPLLSRIAGDRSRVVSPVIDVIDWKTF

QYYPSKDLQRGVLDWKLDFHWEPLPEHVRKALQSPISPIRSPVVPGEVVAMDRHYFQNTGAYDSLMSLRGGENLELSFKA

WLCGGSVEILPCSRVGHIYQNQDSHSPLDQEATLRNRVRIAETWLGSFKETFYKHSPEAFSLSKAEKPDCMERLQLQRRL

GCRTFHWFLANVYPELYPSEPRPSFSGKLHNTGLGLCADCQAEGDILGCPMVLAPCSDSRQQQYLQHTSRKEIHFGSPQH

LCFAVRQEQVILQNCTEEGLAIHQQHWDFQENGMIVHILSGKCMEAVVQENNKDLYLRPCDGKARQQWRFDQINAVDER

What is claimed is:

1. An isolated polynucleotide comprising a polynucleotide sequence set forth in SEQ ID NO:1, wherein said polynucleotide encodes a polypeptide having ppGaNTase-T6 activity.

2. An expression vector comprising a polynucleotide capable of encoding the polypeptide set forth in SEQ ID NO:2, when said expression vector is present in a compatible host cell.

3. A process for producing a recombinant host cell which comprises the step of introducing into a cell an expression vector comprising a polynucleotide capable of encoding the polypeptide set forth in SEQ ID NO:2 such that the host cell, under appropriate culture conditions, produces said polypeptide.

4. A recombinant host cell produced by the process of claim 3.

5. A membrane of the recombinant host cell of claim 4 expressing said polypeptide.

6. A process for producing a polypeptide which comprises culturing the host cell of claim 4 under conditions sufficient for the production of said polypeptide and recovering said polypeptide from the culture.

7. The isolated polynucleotide of claim 1 consisting the polynucleotide set forth in SEQ ID NO:1.

8. An isolated polynucleotide comprising a polynucleotide sequence encoding a polypeptide sequence of SEQ ID NO:2 wherein said polypeptide has ppGaNTase-T6 activity.

9. The isolated polynucleotide of claim 8, that is the polynucleotide encoding the polypeptide of SEQ ID NO:2.

10. An isolated polynucleotide encoding a polypeptide with SEQ ID NO:2 and having ppGaNTase-T6 activity obtained by screening a library under stringent hybridization conditions with a labeled probe having the sequence of SEQ ID NO: 1.

11. An isolated polynucleotide that is fully complementary to an isolated polynucleotide comprising a nucleotide sequence encoding a polypeptide comprising the amino acid sequence set forth in SEQ ID NO:2 wherein said polypeptide has ppGaNTase-T6 activity.

12. The isolated polynucleotide of claim 11 that is fully complementary to the nucleotide sequence set forth in SEQ ID NO:1.

* * * * *